US012685330B2

(12) United States Patent
Nolan et al.

(10) Patent No.: US 12,685,330 B2
(45) Date of Patent: Jul. 21, 2026

(54) COMPOSITION OF A DIETARY SUPPLEMENT AND/OR A NUTRITIONAL ADDITIVE FOR FOOD, A UNITARY DOSAGE FORM OF SAID COMPOSITION, AND THEIR USE FOR IMPROVEMENT OF THE QUALITY OF VISUAL PERFORMANCE INCLUDING CONTRAST SENSITIVITY IN PERSONS IN NEED OF SUCH AN IMPROVEMENT, INCLUDING PERSONS SUFFERING FROM AT LEAST ONE EYE DISEASE, PARTICULARLY VITREOUS FLOATERS

(71) Applicants: ebiga-VISION GMBH, Greifswald (DE); MACIEJ OSEKA 4EYEZ, Warsaw (PL)

(72) Inventors: John Nolan, Carriganore (IE); Emmanuel Ankamah, Carriganore (IE); Maciej Oseka, Warsaw (PL); Robert Kuchling, Berlin (DE)

(73) Assignees: EBIGA-VISION GMBH, Greifswald (DE); MACIEJ OSEKA 4EYEZ, Warsaw (PL)

( * ) Notice: Subject to any disclaimer, the term of this patent is extended or adjusted under 35 U.S.C. 154(b) by 768 days.

(21) Appl. No.: 17/764,053

(22) PCT Filed: Sep. 24, 2020

(86) PCT No.: PCT/PL2020/050069
§ 371 (c)(1),
(2) Date: Mar. 25, 2022

(87) PCT Pub. No.: WO2021/061000
PCT Pub. Date: Apr. 1, 2021

(65) Prior Publication Data
US 2022/0378075 A1     Dec. 1, 2022

(30) Foreign Application Priority Data
Sep. 25, 2019    (PL) ........................................ 431268

(51) Int. Cl.
| A23L 33/175 | (2016.01) |
| A23L 33/105 | (2016.01) |
| A23L 33/15 | (2016.01) |
| A23L 33/16 | (2016.01) |
| A61K 31/198 | (2006.01) |
| A61K 31/375 | (2006.01) |
| A61K 36/752 | (2006.01) |
| A61K 36/87 | (2006.01) |
| A61P 27/02 | (2006.01) |

(52) U.S. Cl.
CPC ........... *A23L 33/175* (2016.08); *A23L 33/105* (2016.08); *A23L 33/15* (2016.08); *A23L 33/16* (2016.08); *A61K 31/198* (2013.01); *A61K 31/375* (2013.01); *A61K 36/752* (2013.01); *A61K 36/87* (2013.01); *A61P 27/02* (2018.01)

(58) Field of Classification Search
CPC ...... A23L 33/175; A23L 33/105; A23L 33/16; A23L 33/15; A61P 27/02; A61K 31/375; A61K 36/752; A61K 36/87
See application file for complete search history.

(56) References Cited

U.S. PATENT DOCUMENTS

| 2007/0286925 A1 | 12/2007 | Zhang et al. |
| 2008/0038367 A1 | 2/2008 | Saloum |
| 2011/0142766 A1 | 6/2011 | Rafanelli |
| 2016/0151437 A1* | 6/2016 | Jiang-Chung ........ A61K 31/341 |
| | | 424/641 |

FOREIGN PATENT DOCUMENTS

| CN | 102348390 A * | 2/2012 | ............. A23L 27/13 |
| EP | 2433640 A1 | 3/2012 | |
| EP | 2138055 B1 | 8/2012 | |
| EP | 2641597 A1 | 9/2013 | |
| EP | 2252285 B1 | 4/2015 | |
| EP | 1701715 B1 | 10/2016 | |
| EP | 2883544 B1 | 9/2018 | |

(Continued)

OTHER PUBLICATIONS

International Search Report in Application No. PCT/PL2020/050069 dated Jan. 13, 2021.
Written Opinion of the International Searching Authority in Application No. PCT/PL2020/050069.
International Preliminary Report on Patentability in Application No. PCT/PL2020/050069 dated Jan. 10, 2022.
Ankamah et al., "Dietary InterventionWith a Targeted Micronutrient Formulation Reduces the Visual Discomfort Associated With Vitreous Degeneration", Translational Vision Science & Technology, Oct. 2021, vol. 10, No. 12, Art. 19, pp. 1-17.
Bishop et al., "Age-Related Changes on the Surface of Vitreous Collagen Fibrils", Apr. 2004, Investigative Ophthalmology & Visual Science, pp. 1041-1046, vol. 45, No. 4.

(Continued)

*Primary Examiner* — Zohreh A Fay
(74) *Attorney, Agent, or Firm* — Wentsler LLC

(57) ABSTRACT

Provided are a composition of a dietary supplement and a nutritional additive for food, a unitary dosage form of said composition, and their use for the improvement of the quality of visual performance including contrast sensitivity. An illustrative composition of the present disclosure includes as active substances L-lysine, vitamin C, zinc, grape extract and bitter orange extract in therapeutically effective quantities, and optionally at least one excipient. In some embodiments, the percentages of the individual active substances relative to the sum of the percentages of all active substances are about 50% by weight of L-lysine, about 15% by weight of vitamin C, about 2% by weight of zinc, about 10% by weight of the grape extract and about 23% by weight of the bitter orange extract, with all percentages of the individual active substances adding up to 100% by weight of all active substances.

11 Claims, No Drawings

(56) References Cited

FOREIGN PATENT DOCUMENTS

PL          406932 A1      8/2015
WO        2015195491      12/2015

OTHER PUBLICATIONS

Cipolletta, et al., "A Psychological Perspective of Eye Floaters", Aug. 21, 2012, Qualitative Health Research, pp. 1547-1558, vol. 22, No. 11.

Delaney et al., "Nd: YAG vitreolysis and pars plana vitrectomy: surgical treatment for vitreous floaters", 2002, Eye, pp. 21-26, vol. 16, No. 1.

Elawadi, et al., "Liquefaction of the Vitreous Humor floaters is a Risk Factor for Lens Opacity and Retinal Dysfunction", 2011, Journal of American Science, pp. 927-936, vol. 7, No. 12.

Guyatt, et al., "Measuring disease-specific quality of life in clinical trials", Apr. 15, 1986, CMAJ: Canadian Medical Association Journal, pp. 889-895, vol. 134, No. 8.

Harocopos et al., "Importance of Vitreous Liquefaction in Age-Related Cataract", Jan. 2004, Investigative Ophthalmology & Visual Science, pp. 77-85, vol. 45, No. 1.

Huang, et al. "Vitreous Floaters and Vision: Current Concepts and Management Paradigms", 2014, Vitreous: in Health and Disease, pp. 771-788.

Lumi, et al., "Ageing of the vitreous: From acute onset floaters and flashes to retinal detachment", Apr. 2, 2015, Ageing Research Reviews, pp. 71-77, vol. 21.

Sendrowski, et al., "Current treatment for vitreous floaters", Mar. 2010, Optometry Journal of the American Optometric Association, pp. 157-161, vol. 81, No. 3.

Smolarek-Kasprzak, et al., "Measuring Visual Function Using the MultiQuity System: Comparison with an Established Device", Dec. 16, 2014, Journal of Ophthalmology, pp. 1-7, vol. 2014.

Wagle, et al., "Utility Values Associated With Vitreous Floaters", Jul. 2011, American Journal of Ophthalmology, pp. 60-65, vol. 152, No. 1.

Wilkinson, "Safety of Vitrectomy for Floaters—How Safe is Safe?", Jun. 2011, American Journal of Ophthalmology, pp. 919-920, vol. 151, No. 6.

Yonemoto, et al. "Age of onset of posterior vitreous detachment", 1994, Graefe's Archive for Clinical and Experimental Ophthalmology, pp. 67-70, vol. 232.

Zou, et al., "The impact of persistent visually disabling vitreous floaters on health status utility values", 2013, Quality of Life Research, pp. 1507-1514, vol. 22, No. 6.

Search Report dated Apr. 20, 2020 in Polish Patent Application No. P.431268 (with English-language translation).

"Dietary Supplement—Vitroft, Capsules, 30", https://web.archive.org/web/20150424220644/ https://www.doz.pl/apteka/p54998-vttroft kapsulki 30 szt, Publication Archived on May 24, 2015 (with English-language translation).

"Vitreo x 30 Capsules", https://web.archive.org/web/201706061852 11 /https://www.i-apteka.pl/product-pol-42551-vitreo-x-30-kapsulek. html , Publication archived on Jun. 6, 2017 (with English-language translation).

Kara et al., "Protective Effect of Hesperetin and Naringenin against Apoptosis in Ischemia/Reperfusion-Induced Retinal Injury in Rats", Jan. 30, 2014, The Scientific World Journal, 8 pages, vol. 2014.

Stohs et al., "Effects of p-Synephrine alone and in Combination with Selected Bioflavonoiods on Resting Metabolism, Blood Pressure, Heart Rate and Self-Reported Mood Changes", Apr. 28, 2011, International Journal of Medical Sciences, pp. 295-301, vol. 8, No. 4.

Stohs, "Safety, Efficacy, and Mechanistic Studies Regarding *Citrus aurantium* (Bitter Orange) Extract and p-Synephrine", Jul. 28, 2017, Phytotherapy Research, pp. 1463-1474, vol. 31.

Suntar et al., "An Overview on *Citrus aurantium* L.: Its Functions as Food Ingredient and Therapeutic Agent", May 2, 2018, Oxidative Medicine and Cellular Longevity, 12 pages, vol. 2018.

* cited by examiner

COMPOSITION OF A DIETARY SUPPLEMENT AND/OR A NUTRITIONAL ADDITIVE FOR FOOD, A UNITARY DOSAGE FORM OF SAID COMPOSITION, AND THEIR USE FOR IMPROVEMENT OF THE QUALITY OF VISUAL PERFORMANCE INCLUDING CONTRAST SENSITIVITY IN PERSONS IN NEED OF SUCH AN IMPROVEMENT, INCLUDING PERSONS SUFFERING FROM AT LEAST ONE EYE DISEASE, PARTICULARLY VITREOUS FLOATERS

FIELD OF THE INVENTION

The invention concerns a composition of a dietary supplement and/or a nutritional additive for food comprising as active substances L-lysine, vitamin C, zinc, grape extract and bitter orange extract in therapeutically effective quantities according to the claims.

The subject-matter of the invention is also a unitary dosage form comprising said composition of the dietary supplement and/or the nutritional additive for food.

The subject-matter of the invention is, furthermore, a use of the above-mentioned composition and unitary dosage form for improvement of the quality of visual performance including contrast sensitivity in persons in need of such an improvement and for improvement of the quality of life of these persons, including persons, which were diagnosed to suffer from at least one eye disease, and in particular from vitreous floaters.

BACKGROUND OF THE INVENTION

In the state of the art, there are several known dietary supplements, which comprise combinations of various ingredients, for use in eye diseases.

The studies conducted in recent decades indicate a positive impact of nutritional factors in the prevention and treatment of eye diseases. Among the best-known effects nowadays, there is the effect of L-lutein and zeaxanthin, natural carotenoids, which are ingredients contained in many food products of plant origin, in the prevention and treatment of the age-related macular disease (AMD or ARMD). As studies show, lutein and zeaxanthin form part of the macular pigment, which protects the macula lutea from the negative impact of light, in particular of the highly energetic ultraviolet radiation.

Patent specification EP 2883544 B1 informs that the oral application of the dietary supplement in the form of a preparation comprising lutein, zeaxanthin along with other nutritional ingredients supports the increase of the optical density of the macular pigment (MPOD), may protect the eye retina from the negative impact of light radiation, and may inhibit the development of the age-related macular disease, AMD.

As confirmed in patent specification EP 2138055 B1, the oral application of the dietary supplement in the form of a preparation comprising lutein, zeaxanthin along with other nutritional ingredients supports also the improvement of eye functions.

According to the explanations contained in patent specification EP 1701715 B1, the oral application of the dietary supplement comprising various nutritional ingredients, among others zeaxanthin, vitamin C, vitamin E and zinc, has a positive impact on patients suffering from AMD, and in particular on those patients which are in the so-called "geographic atrophy" stage of this disease or a comparable stage of another eye disorder.

Patent document EP 2433640 A1 teaches that lutein and zeaxanthin along with the superoxide dismutase (SOD) protect eye photoreceptors against the damaging impact of the ultraviolet radiation.

As disclosed in EP 2252285 B1, a positive impact of nutritional ingredients on eye parameters was also found in other eyesight diseases such as glaucoma for instance. The oral application of a nutritional supplement preparation available under trade name Pycnogenol®, which contains an extract from a maritime pine *Pinus pinaster* or *Pinus maritima*, along with other nutritional factors leads to decreased intraocular pressure and may at the same time support a decreased risk of developing glaucoma.

In patent document EP 2641597 A1, it was indicated that the oral application of the eicosapentaenoic acid (EPA) and/or the docosahexaenoic acid (DHA) affects the improvement of the ability to see in the dry eye syndrome.

The above data indicate that various nutritional ingredients have a positive impact with respect to improving the ability to see in various eye disorders such as AMD, glaucoma or dry eye syndrome.

In the light of the known studies and disclosures from the state of the art, and in connection with the fact that the aetiology of each eye disease is different, it is a key issue that ingredients contained in food preparations and/or dietary supplements meant for preventing, treating or inhibiting eye disease development are composed in such a way that they counteract the initial causes underlying a certain eye disorder.

Vitreous floaters are another of the above-mentioned eye diseases of a growing significance in recent years. This eye disorder affects the vitreous body of the eye and leads to deepening degeneration in this eye organ. The disease can be extremely bothersome for patients, causing significant difficulties in everyday life. If left untreated, it progresses, serves as a precursor for the development of other accompanying eye diseases, and causes ever-increasing disability of the patients.

Understanding the perspective of the patients suffering from vitreous floaters and the impact of the symptoms of the disease on their assessment of the quality of life is one of issues recently addressed in medical practice. This is because it has been proven that disease symptoms reported by the patients are particularly essential for clinical trials (Guyatt, G. H., C. Bombardier, and P. X. Tugwell, "Measuring disease-specific quality of life in clinical trials", CMAJ: Canadian Medical Association Journal, 1986. 134 (8): p. 889).

However, none of the patent documents from the state of the art pertains in detail to the eye disease such as vitreous floaters, nor mentions nutritional ingredients or pharmaceutical preparations for oral application which could have a therapeutically effective influence on the treatment of this disease, its inhibition or prevention.

To present the development mechanism of this eye pathology, it needs to be explained that the posterior segment of the human eye houses a uniformly transparent gel of a complex structure, an extracellular matrix made up in 99% of water and collagen, proteins and hyaluronic acid, forming an eye organ called the vitreous body. The total volume of the human vitreous body is about 4 ml. A small number of cells, mainly hyalocytes, astrocytes and glial cells physiologically present in the vitreous body, are located in the area of the cortex of the vitreous body. The vitreous body constitutes structural support to the eyeball occupying it up to ¾. Thanks to its transparency it allows unhindered transmission of light. The vitreous body conditions the lucidity of the interior of the eyeball, it is responsible for the shape of the eyeball and maintains the correct intraocular pressure. Along with ageing and/or accompanying diseases and/or because of injuries, from a stable extracellular matrix of the vitreous body, collagen fibres get dissociated from hyaluronic acid and aggregated as clumps, forming watery spaces or lacunae containing hyaluronic acid and water.

Development mechanisms of vitreous floaters include connective tissue disorders, which consist in the combination of collagen fibre proteins of the vitreous body under glycation and oxidative stress, and increased proteolytic activity of enzymes in the vitreous body (Bishop, P. N., et al., "Age-related changes on the surface of vitreous collagen fibrils", Investigative ophthalmology & visual science, 2004. 45(4): p. 1041-1046) (Harocopos, G. J., et al., "Importance of vitreous liquefaction in age-related cataract", Investigative ophthalmology & visual science, 2004. 45(1): p. 77-85).

Bundles of clustered collagen fibres form moveable turbidities called vitreous floaters, which are perceived by the patients as "flies", "webs", "clouds" or "shadows" within the visual field, the severity of which usually gets intensified when moving the head or eyes.

The severity of vitreous floaters depends also on their size and density, distance from the retina and the visual axis, and the width of the pupil. Vitreous floaters disperse light causing blurred vision or haze and increase sensitivity to glare. Vitreous floaters appearing near or within the optical axis of the eye impair vision and, as a consequence, impact negatively on important daily life activities, such as reading, working on a computer, watching objects particularly in the open air in good light conditions, driving a car, and near-work activities. As a result, both the quality of visual performance is reduced, as well as the quality of life of persons suffering from the degeneration of the vitreous body (Huang, L. C., et al., Erratum: "Vitreous Floaters and Vision: Current Concepts and Management Paradigms", in Vitreous, 2014, Springer. p. E1-E2) (Yonemoto, J., et al., "The age of onset of posterior vitreous detachment". Graefe's archive for clinical and experimental ophthalmology, 1994. 232(2): p. 67-70) (Lumi, X., et al., "Ageing of the vitreous: from acute onset floaters and flashes to retinal detachment", Ageing research reviews, 2015. 21: p. 71-77.

Vitreous floaters disturb the quality of vision and negatively impact the quality of life.

Patients have described vitreous floaters as a nuisance which decrease their life comfort (Cipolletta, S., A. Beccarello, and A. Galan, "A psychological perspective of eye floaters", Qualitative health research, 2012. 22(11): p. 1547-1558) (Zou, H., et al., "The impact of persistent visually disabling vitreous floaters on health status utility values", Quality of Life Research, 2013. 22(6): p. 1507-1514).

Quality of life assessment in patients with vitreous floaters measured by the impact of certain symptoms on daily functioning have revealed that vitreous floaters decrease life comfort, to a degree comparable to AMD, diabetic retinopathy, glaucoma, a light version of angina pectoris, a light stroke, colon cancer and asymptomatic HIV. Interestingly, the patients are willing to trade 1,1 years of every 10 years of their remaining life to get rid of the vitreous floaters (Wagle, A. M., et al., "Utility values associated with vitreous floaters", American journal of ophthalmology, 2011. 152(1): p. 60-65. e1.).

Conventional treatment usually offered to the patients with floaters of the vitreous body boils down to reassuring them that with time they will get accustomed to the presence of the floaters and counselling them to adapt to their new visual experience (Sendrowski, D. P. and M. A. Bronstein, "Current treatment for vitreous floaters", Optometry Journal of the American Optometric Association, 2010. 81(3): p. 157-161).

It often happens after ophthalmologists exclude the connection between the presence of vitreous floaters and the diseases of the retina. A surgical treatment which consists in removing part or whole vitreous body may have complications, such as retinal detachment, cataract, glaucoma, haemorrhage to the chamber of the vitreous body and macula oedema. Other treatment methods include laser vitreolysis performed with a neodymium-doped yttrium aluminum laser (Nd-YAG) and administering eye drops, but their effectiveness and safety have not been unequivocally proven (S A, A. and A. Elawadi, "Liquefaction of the Vitreous Humor floaters is a Risk Factor for Lens Opacity and Retinal Dysfunction", Journal of American Science, 2011. 7(12)) (Wilkinson, C. P., "Safety of Vitrectomy for Floaters—How Safe is Safe?", American Journal of Ophthalmology, 2011. 151(6): p. 919-920. e1) (Delaney, Y., A. Oyinloye, and L. Benjamin, "Nd:YAG vitreolysis and pars plana vitrectomy: surgical treatment for vitreous floaters", Eye, 2002. 16(1): p. 21).

In the past, the patients with vitreous floaters were sometimes prescribed eye drops containing potassium iodide, which was believed to have antioxidant properties. There were also attempts to apply enzymes such as the ceruloplasmin to treat floaters with enzymatic vitreolysis, which, however, required eye injections and caused many undesired side effects.

In the state of the art, there are various known compositions of dietary supplements, which comprise combinations of various nutritional ingredients, for use in eye diseases.

However, there are no known preparations for oral administration or compositions of dietary supplements, which would contain all the below-mentioned active substances used in the composition of the dietary supplement according to the present invention or which would present properties of these below-mentioned active substances and would be meant for treating eye diseases, slowing down or inhibiting their development or preventing them.

There are no known preparations for oral administration or compositions of dietary supplements, which would be meant in particular for treating vitreous floaters, slowing down or inhibiting their development and preventing their appearance.

Also, there are no known compositions of dietary supplements meant for the patients with vitreous floaters with proven evident and direct impact on the objective and subjective assessment of the quality of visual performance in these patients.

OBJECTIVES OF THE PRESENT INVENTION

Therefore, it is desired to provide a composition of a dietary supplement, which would ensure complex support of eye functions by improving the subjective assessment of the quality of life in persons suffering from eye diseases or persons jeopardized with the possible development of eye diseases, and by improving the ability to see.

In the light of the ever-increasing importance of eye diseases including the vitreous floaters disease, the inventors of the present invention have also noticed the need to develop a composition of a dietary supplement meant for persons suffering from eye diseases, and in particular for persons suffering from vitreous floaters, to treat these diseases, to slow down their development or to inhibit them, and to prevent their appearance.

Because vitreous floaters are nowadays a very common issue, the inventors of the present invention have launched research aiming at development of a composition of a dietary supplement and its dosage regime which would ensure improving the subjective assessment of the quality of life in persons with eye diseases, and in particular in persons with vitreous floaters, as well as improving the quality of visual performance in these persons measured by objective study methods.

These aims were reached with the composition of the dietary supplement according to the present invention, whereas it has unexpectedly turned out that simultaneous inclusion in the composition of L-lysine, vitamin C, zinc, the grape extract and the bitter orange extract significantly improves the subjective assessment of the quality of life in persons suffering from vitreous floaters, and the objective assessment of the quality of visual performance measured with the contrast sensitivity.

SUMMARY OF THE PRESENT INVENTION

A composition of a dietary supplement and/or nutritional additive for food according to the present invention contains as active substances L-lysine, vitamin C, zinc, grape extract and bitter orange extract in therapeutically effective quantities, and potentially at least one excipient.

The percentages of individual active substances of the composition relative to a sum of percentages of all active substances are:

a) about 50% by weight of L-lysine,
b) about 15% by weight of vitamin C,
c) about 2% by weight of zinc,
d) about 10% by weight of the grape extract,
e) about 23% by weight of the bitter orange extract, with all percentages of the individual active substances adding up to 100% by weight of all active substances.

Preferably, the composition contains:

a) from about 125 mg to about 250 mg of L-lysine,
b) from about 40 mg to about 80 mg of vitamin C,
c) from about 5 mg to about 10 mg of zinc,
d) from about 25 mg to about 50 mg of the grape extract,
e) from about 60 mg to about 120 mg of the bitter orange extract.

Preferably, the ingredients of the composition constitute a mixture.

Preferably, the grape extract and/or the bitter orange extract is selected from the group comprising the extract from fruit seeds, the extract from grape pulp, the extract from grape skin, the extract from blossoms of these plants, or their combinations.

Preferably, the grape extract is a grape extract of the *Vitis vinifera* species and/or the bitter orange extract is a bitter orange extract of the *Citrus aurantium* species, preferably, both extracts DER 100:1.

Preferably, the excipient is a substance nutritionally permitted and is selected from the group comprising at least a vehicle agent, a bulking agent, a binding agent, a disintegrant, a surfactant, a lubricant, an anti-caking agent, an acidity regulator, an antioxidant, a synthetic and/or natural colourant, a colour retaining substance, an emulsifier, a sweetener, an aromatizing agent, a flavouring agent, a flavour enhancer, a preservative, a stabilizing agent, a solvent and a diluent, or their mixtures.

Preferably, the composition has a form of any formulation adequate for oral application such as a powder or a granulate or a liquid or a gel.

Preferably, the composition is applied in a preferred dose, frequency and form for a period of at least 2 months, preferably for a period of at least 3 months and more preferably for a period of at least 6 months.

A unitary dosage form according to the present invention contains the composition of the dietary supplement and/or nutritional additive for food according to the present invention.

Preferably, the unitary dosage form contains a daily dose of the active substances of the present composition.

Preferably, the unitary dosage form has a form selected from the group comprising at least a capsule, a tablet, a sachet, a "stick-type" sachet and an ampoule, including any of these forms ensuring a prolonged release of the active substances of the composition in time of at least 3 hours after consumption.

A composition of the dietary supplement and/or nutritional additive for food and a unitary dosage form, according to the present invention, are characterized in that they are meant for use with the objective to improve quality of visual performance including contrast sensitivity in persons in need of such an improvement and to improve quality of life of these persons.

A composition of a dietary supplement and/or nutritional additive for food and a unitary dosage form according to the present invention, are characterized in that they are meant for use in treating eye diseases and/or slowing down and/or inhibiting their development and/or preventing them.

Preferably, the composition and the unitary dosage form according to the present invention, are characterized in that they are meant for the use in persons suffering from vitreous floaters.

A use of the composition of the dietary supplement and/or nutritional additive for food and the unitary dosage form according to the present invention, for improvement of quality of visual performance including contrast sensitivity in persons in need of such an improvement and for improvement of quality of life of these persons.

A use of the composition of the dietary supplement and/or nutritional additive for food and the unitary dosage form according to the present invention, for treating eye diseases and/or slowing down and/or inhibiting their development and/or preventing them.

Preferably, the use of the composition and the unitary dosage form according to the present invention, is characterized in that it is meant for persons suffering from vitreous floaters.

The term "the extract of" used in the specification of the present invention means a condensed plant preparation, which is obtained by pickling the plant raw material with a solvent. The extract may be condensed up to the state when the solvent is completely removed. Suitable extracts are available on the market, but they may be also produced with methods known in the field of plant extracts preparation.

In one of embodiments of the composition of the dietary supplement according to the present invention, the grape extract is a grape extract of *Vitis vinifera* species DER 100:1 and the bitter orange extract is a bitter orange extract of *Citrus aurantium* species DER 100:1. "DER" means drug extract ratio, which is a ratio of the quantity of the plant raw material used for producing the plant extract to the quantity of the obtained plant extract. A person skilled in the art of plant extract production will notice that it is also possible to use appropriate extracts from other species of the above-defined plants and that it is also possible to use extracts with other DER values.

In the specification of the present invention, the term "excipient" is to be understood widely as one substance or a greater number of substances or their mixtures, which are usually used for producing typical compositions of dietary supplements and/or nutritional additives for food, also including beverages, and/or for producing typical pharmaceutical compositions.

The excipient may be, thus, any substance nutritionally acceptable which is, however, as well as its content in the composition of the dietary supplement according to the present invention, selected respectively to the active substance content in that composition and to the formulation of that composition and to the unitary dosage form according to the present invention, as well as respectively to production methods of the composition, the formulation and the unitary dosage form according to the present invention. The choice of the suitable excipients constitutes knowledge of an average person skilled in the art of formulating compositions of dietary supplements and/or pharmaceutical compositions.

The composition of the dietary supplement and/or nutritional additive for food according to the present invention may be the formulation in any form suitable for consumption and adequate for oral administration by a human.

Preferably, the composition of the dietary supplement and/or nutritional additive for food according to the present invention is the formulation in the form of a powder or a granulate. For obtaining such formulations of this composition, the ingredients of the composition, that is the active substances and the excipients if they are contained in the composition, are subjected to normal mixing or granulation with techniques known to the person skilled in the art of pharmacy.

The composition of the dietary supplement and/or nutritional additive for food according to the present invention may be the formulation in any form suitable for drinking such as liquid or gel.

The formulations for oral administration or produced from the composition according to the present invention, which have the form of a powder or a granulate or a liquid or a gel, are subsequently used for producing the unitary dosage form.

Various forms of the formulation of the composition according to the present invention respectively contained and/or closed in a casing for the unitary dosage form such as a capsule, a tablet, a sachet, a "stick-type" sachet or an ampoule, may, preferably, require to be stirred in water or a beverage or another liquid before consumption according to the needs of a patient or according to her/his taste preferences.

Some of the active substances of the composition may be given the form of a powder or a granulate or a liquid or a gel by grinding or granulation or liquefaction or gelling, and then be closed, for instance, in microcapsules, before their inclusion into the final formulation form ready for being consumed and before producing the unitary dosage form of the composition according to the present invention.

Preferably, the unitary dosage form of the composition of the dietary supplement and/or nutritional additive for food according to the present invention contains a daily dose of the active substances of the present composition. Such a unitary dosage form according to the present invention filled with the composition according to the present invention allows the use of the unitary dosage form once a day and simultaneously obtaining the desired therapeutic effect.

The unitary dosage form in the context of the present invention is meant for oral administration. Therefore, preferably, the unitary dosage form has a form selected from the group comprising at least a capsule, a tablet, a sachet, a "stick-type" sachet and an ampoule, including any of these forms ensuring a prolonged release of the active substances of the composition in time of at least 3 hours after consumption.

The production of the unitary dosage forms according to the present invention with the composition of the dietary supplement and/or nutritional additive for food according to the present invention are technological operations known in the pharmaceutical technology and are realized using standard instruments.

The selection of the active substances in the composition of the dietary supplement and/or nutritional additive for food according to the present invention was made by the inventors basing on the knowledge about pathomechanisms of the development of vitreous floaters and potential substances inhibiting these mechanisms. Substances having properties required in the present invention were selected basing on the evidence from in vitro studies as well as the knowledge of the impact of these substances on the physiological functions of other organs in the human body.

As the two main pathomechanisms behind the creation of vitreous floaters are oxidative stress and glycation of collagen fibres of the vitreous body, the active substances of the composition have been selected accordingly—those which decrease intravitreal oxidative stress, which means that they have antioxidant properties and neutralize free radicals in aqueous environment, that is vitamin C and zinc, as well as substances which strongly hamper the glycation of collagen fibres and decrease the activity of enzymes responsible for collagen disintegration, that is L-lysine, the grape extract and the bitter orange extract.

L-lysine is an essential amino acid, which needs to be obtained from food as the human organism cannot produce it, and which among others supports the creation of collagen. L-lysine is the free form of this essential amino acid and is absorbed directly into the bloodstream.

The extracts from grapes and bitter orange contain great quantities of biologically active chemical compounds called oligomeric proanthocyanidin complexes or oligomeric proanthocyanidins (OPC), which are commonly known as "super antioxidants" due to their strong antioxidant properties and properties of hampering activity of proteases breaking collagen fibres.

Proanthocyanidins are known also as bioflavonoids and contain hesperidin in high concentrations, which has, apart from antioxidant properties, also anti-inflammatory and protective properties on blood vessels, thereby improving the state of capillaries as well as decreasing their permeability.

In the preferred embodiment of the composition according to the present invention, for the grape extract a grape extract of the *Vitis vinifera* species was chosen and for the bitter orange extract a bitter orange extract of the *Citrus aurantium* species.

The formulations of the composition according to the present invention in the form of the powder or the granulate or the liquid or the gel subsequently serve to produce the unitary dosage form.

Preferably, various forms of the formulation of the composition according to the present invention are placed in the casing or the sheath to obtain the unitary dosage form in the form of the capsule for instance.

After the selection of the active substances for the ingredients of the composition, the inventors matched the percentages by weight of the individual active substances relative to the sum of the percentages by weight of all five active substances, taking into account the guidelines concerning the quantity of the individual active substances for dietary supplements and doses of dietary supplements, which quantities have to reflect the content of the individual active substances in natural or food products and cannot exceed the acceptable quantities and doses for a dietary supplement.

Then, the powdered active substances in the respective percentages by weight were used to prepare the mixture, which was closed in the unitary dosage form in the form of the capsule. One capsule contained 125 mg of L-lysine, 40 mg of vitamin C, 5 mg of zinc, 25 mg of the grape extract of the *Vitis vinifera* species DER 100:1 and 60 mg of the bitter orange extract of the *Citrus aurantium* species DER 100:1. Such capsules were administered to persons from the active group in the course of the studies conducted as described below in the preferred embodiment of the present invention.

The unitary dosage forms may contain also other doses of the composition according to the present invention, including the daily dose of the active substances contained in the composition, subject to requirements concerning dietary supplements.

The present invention foresees the use of different formulation forms adequate for oral application for the composition according to the present invention and different forms of the unitary dosage form, as well as different doses of the active substances of the present composition in the unitary dosage form. Thanks to that, after the doctor has determined a therapeutically effective dose of the composition according to the present invention for each patient at a specific stage of therapy or prevention, the patient will be able to apply the unitary dosage form suitable for her/him with the suitable dose of the composition. In this context, it is worth mentioning that small doses of the composition according to the present invention may be applied preferably in the beginning and the dosage may be gradually increased up to the point when a clear positive impact is observed on the subjective assessment of the quality of life given by the patient with a given eye disease and/or on the objective parameters of the quality of visual performance in this patient. On the flip side, high doses of the composition according to the present invention could be administered initially and gradually decreased up to the point when a subjective or objective improvement in visual performance is achieved for the given patient.

When it comes to the dietary supplementation period required to evoke a measurable improvement of the subjective assessment of the quality of life and of the objective assessment of the ability to see in persons with vitreous floaters, it depends on a number of factors, including the state of the development of the disease and the state of the general health of the patients before the commencement of the dietary supplementation as well as on the administered daily dose of the composition according to the present invention. The studies conducted show that to elicit an improvement, dietary supplementation with the composition according to the present invention is required for at least 8 weeks, and more preferably for at least 3 to 6 months before the contrast sensitivity is measured following the supplementation.

The inventors of the present invention have attempted to study the effects of the supplementation with the composition according to the present invention on the subjective assessment of the quality of life changes in patients with vitreous floaters and on the changes in objective visual performance parameters in these persons, especially changes in sensitivity to contrast. The visual performance quality parameters are objective parameters which assess the ability to see because they are tested with objective methods of assessment on special medical devices.

For the subjective assessment of the quality of life of persons with vitreous floaters, specifically for the need of this inventive project, a non-standard questionnaire was prepared for each individual patient to complete pre and post supplementation with the composition according to the present invention. The content of the questionnaire has been presented below towards the end of the present description. The questionnaire allowed study participants to classify their assessment of the feelings regarding the quality of visual performance since it served to capture the subjective responses of the patients with vitreous floaters regarding the severity of the disease and its impact on their daily functioning.

Among the objective parameters of the quality of visual performance, for the purposes of this inventive project, the parameter called contrast sensitivity was chosen for examination in this study. Contrast is the difference in visual properties which makes an object or its pictorial representation discernable from other objects and the background. In the visual perception of the real world, the contrast is determined by the difference in colour and the brightness of the object and other objects within the same visual field. Contrast sensitivity is a measurement of the sensitivity of an individual towards changes in contrast and is indispensable for detecting an object as being separate from the background.

Changes in the value of this parameter correlate well with changes in the quality of visual performance including i.a. recognition of object contours and their details in the visual field and recognition of object contours and their details in the conditions of variable lighting.

The inventors unexpectedly concluded that the consumption of the dietary supplement and/or nutritional additive for food according to the present invention improves the subjective assessment of the life quality in persons with vitreous floaters. The positive subjective assessment of the life quality in these persons has been again quite unexpectedly supported by objective eye-sight tests, that is the improvement of sensitivity to contrast.

The present invention provides the composition of nutritional substances for oral application, which positively affects the quality of eye-sight and sensitivity to contrast in persons with vitreous floaters.

Short Description of Tables

The present invention shall be further described by presenting the preferred embodiment of its realization and with reference to the Tables, which present:

Table 1 presents changes in the frequency of reported disturbances caused by the vitreous floaters in the control group and the active group after 6 months of supplementation, Table 2 presents changes in the assessment of the impact of vitreous floaters on the daily life in the control group and the active group after 6 months of supplementation, and Table 3 presents the comparison of the changes in visual functions in the active and control groups before and after supplementation.

PREFERRED EMBODIMENT OF THE PRESENT
INVENTION 61 patients suffering from vitreous floaters were randomized in a 50:50 fashion into the active group (n=31) or the control group (n=30). The active group received the composition according to the present invention formulated as the mixture from the powdered active substances in respective percentages by weight and closed in the unitary dosage form in the form of the capsule. One capsule contained 125 mg of L-lysine, 40 mg of vitamin C, 5 mg of zinc, 25 mg of the *Vitis vinifera* grape extract DER 100:1 and 60 mg of the *Citrus aurantium* bitter orange extract DER 100:1. The patients from the active group consumed the composition according to the present invention in the amount of one capsule a day for 6 months. The control group received a placebo capsule containing microcrystalline cellulose which had similar shape and colour to the capsule containing the tested composition according to the present invention.

For the subjective assessment of the impact of vitreous floaters on quality of life at the baseline and at the end of the study, a customized, non-standardized questionnaire on visual disturbances caused by vitreous floaters was employed, as presented below towards the end of the present description.

The contrast sensitivity parameter (Multiquity LogCS Score), which is an objective assessment parameter of the quality of visual performance, was measured for each patient before and after supplementation, using the MiQ Contrast 256 test, Smolarek-Kasprzak, P., et al., "Measuring visual function using the MultiQuity system: Comparison with an established device", Journal of ophthalmology, 2014. Binocular contrast thresholds (%) in photopic and mesopic conditions were measured with the Acuity-plus test from the Advanced Vision and Optometric Test (AVOT). Retinal function (rods and cones) was assessed with the Flicker-plus test from the AVOT suite, which employs a 15 Hz flicker stimulus. Macular Pigment (MP) was measured with the use of the multi-colour Heidelberg Spectralis HRA+OCT test from Heidelberg Engineering GmbH, Heidelberg, Germany.

For the assessment of the safety of the composition according to the present invention on the organisms of the patients, apart from the clinical studies, also biochemical blood tests were performed, that is a complete blood morphology and biochemistry of the blood serum.
Alterations in the Increase of Vitreous Floaters Disturbances in the Course of 6 Months of Supplementation To assess the degree of the increase in changes connected with vitreous floaters in the subjective perception of the patients, they were asked about visual disturbances caused by floaters in the course of past 6 months prior to enrolment into the study (baseline visit) and following six months of supplementation (final study visit). The question offered a 3-response choice, which was scored as follows: My condition has been stable and I have not been bothered by my floaters—0, My floaters have been observed intermittently/were moderately bothersome—3, My floaters have been consistently bothersome—6. A score of 3 signified a moderate increase in the symptoms, with increasing severity denoted by a progress towards a score of 6.

At baseline, the median score (IQR, Interquartile Range) for both the control as well as active groups was 3.00 (3.00-6.00) and did not differ significantly (p=0.689; Mean±SD score of 3.69±1.54 and 3.90±1.40 for the control and active groups, respectively). Following supplementation, the median score (IQR) recorded was 3.00 (3.00-6.00) and 3.00 (0.00-3.00) for the control and active groups, respectively, the difference between them being statistically significant (p=0.018; Mean±SD score of 3.35±1.96 and 2.10±1.79 for the control and active groups, respectively).

At baseline, in the control group 1 subject (3.85%) reported being stable and not feeling the presence of floaters, 20 subjects (73.07%) reported occasional disturbances caused by their floaters, and 9 subjects (23.08%) reported being constantly bothered by their floaters. Following supplementation, 4 subjects (15.38%) reported that they have not paid attention to their vitreous floaters after the follow-up visit (p=0.564) whereas 7 subjects (26.92%) reported being constantly bothered by their floaters. The 11.53% increase was thus noted in the category "no bother from floaters", and the 3.84% increase in the category "persistent disturbances from floaters", for the control group after supplementing for 6 months.

In summary, for the control group the self-reported results of the subjects proved that the state of 14 subjects (53.85%) remained without changes, the state of 7 subjects (26.92%) improved, and the state of 5 subjects (19.23%) deteriorated, in the supplementation time from the baseline until the final visit.

In the active group, which was supplemented with the composition according to the present invention, at baseline 1 subject (3.33%) reported being stable and not feeling the presence of floaters, 20 subjects (66.67%) reported moderate disturbances from their floaters, and 9 subjects (30%) reported that the floaters were constantly bothersome prior to enrolment into the study. After supplementation for 6 months, 11 subjects (36.67%) reported that they do not feel the presence of floaters (p=0.001). Also, 2 subjects (6.67%) reported being constantly bothered by their floaters following supplementation. As a result, there was the increase of 33.34% in the number of the patients reporting the lack of floaters, and the decrease of 23.33% in the number of the patients reporting constant disturbances from floaters after the 6-month supplementation period. In summary, for the active group, the results reported by the patients proved that the state of 12 subjects (40%) remained without changes, the state of 16 subjects (53.33%) improved, and the state of 2 subjects (6.67%) deteriorated, in the time between the baseline visit and the visit after 6 months of supplementation. See Table 1 below.

TABLE 1

Changes in the frequency of reported disturbances from vitreous floaters in the control and active groups after 6 months of supplementation

|  | Control Group (placebo) - number of tested patients | Active Group (supplemented with the composition according to the present invention) - number of tested patients |
|---|---|---|
| Without changes | 14 | 12 |
| Improvement | 7 | 16 |
| Deterioration | 5 | 2 |

Change in the Assessment of the Impact of Vitreous Floaters on Daily Life in the Control and Active Groups after 6 Months of Supplementation The study assessed the impact of vitreous floaters on the daily life of the patients before and after the 6-month supplementation on a 5-point scale: no impact, a small impact, a moderate impact, a great impact and a very significant impact, and this impact was assessed on the scale from 0 to 4, with 4 reflecting the very significant impact, and 0 no impact. At baseline, the impact of floaters on the daily life of the subject was assessed a week before the beginning of supplementation. After supplementation, the same questions were posed again at the final visit to assess the impact of floaters on the daily life of the subjects a week prior to the visit. An improvement for a participant was defined as a lesser score at the final visit in comparison with the score obtained during the baseline visit.

At baseline, the same median score (IQR) of 1.00 (0.00-2.00) was noted for both groups (p=0.407; Mean±SD score of assessment 1.08±0.85 and 1.37±1.27 for the control and active groups, respectively). Following supplementation, the median scores reported were 1.00 (0.00-2.00) and 0.50 (0.00-1.00) for the control and active groups (p=0.302), respectively. Within group comparisons of the baseline and final scores revealed a statistically significant difference for the active group (p=0.003) but not for the control group (p=0.658).

When asked about the impact of floaters on their daily life a week prior to the study, 7 subjects from the control group and 9 subjects from the active group reported no impact of their floaters on their daily life. Following supplementation, 10 subjects in the control group reported the lack of impact of floaters on their daily life and this difference was not statistically significant (p=0.658). Within the active group, however, 14 subjects reported no impact of floaters on their daily life post supplementation and this improvement was statistically significant (p=0.003). In summary, for the control group the results reported by the patients proved that the state of 13 subjects (50%) remained without changes, the state of 7 subjects (26.92%) improved, and the state of 6 subjects (23.08%) deteriorated in the 6-month study period. For the active group, the results reported by the patients proved that the state of 14 subjects (46.67%) remained without changes, the state of 14 subjects (46.67%) improved, and the state of 2 subjects (6.67%) deteriorated in the 6-month supplementation period between the baseline and the final visits. See Table 2 below.

TABLE 2

Change in the assessment of the impact of vitreous floaters on daily life in the control and active groups following 6 months of supplementation

|  | Control Group (placebo) - number of tested patients | Active Group (supplemented with the composition according to the present invention) - number of tested patients |
| --- | --- | --- |
| Without changes | 13 | 14 |
| Improvement | 7 | 14 |
| Deterioration | 6 | 2 |

Impact of Vitreous Floaters on Certain Activities in the Control and Active Groups After 6 Months of Supplementation The impact of vitreous floaters on certain activities: reading small letters (drugs or cosmetics information leaflets), reading newspapers or books, driving a car during the day, using a computer or a mobile phone, watching TV was assessed before the commencement of the study at the baseline visit and after the end of the study at the final visit by subjects responding with either "Yes" or "No" to each activity. A "Yes" response for a certain activity meant disturbances caused by vitreous floaters during this activity.

A positive response was scored 1, a negative 0. An overall activity score was calculated by summing up and averaging the individual activity scores reported by each participant of the study. The median overall activity score was determined for each tested group at the baseline and final visits, compared between the groups and within the groups pre and post supplementation.

At baseline, the median overall activity scores (IQR) were 0.40 (0.10-0.80) and 0.60 (0.30-0.80) for the control and active groups (p=0.104), respectively. Following supplementation, the median overall activity scores were 0.20 (0.00-0.50) and 0.20 (0.00-0.60) for the control and active groups (p=0.619), respectively. Comparing the baseline and final overall activity scores within both groups, there was a statistically significant difference (p=0.007) in median overall activity score for the active group after 6 months of supplementation, with a lesser score recorded at the final visit (where the lesser score indicates less activities affected by floaters). The difference observed in the control group was, on the other hand, not statistically significant (p=0.064).

Subjective Severity of Floater Disturbances Categorized by Age, Sex or PVD Status, Before and After Supplementation in the Active Group To assess the influence of demographic factors on the application of the supplementation, the active group was stratified by age, sex and posterior vitreous detachment (PVD) status.

With a median age of 56.5 years, the participants of the study were divided into two age groups: 55 years and below (n=12), and beyond 55 years (n=18), and the severity of their floater disturbances in the groups were compared before and after supplementation.

Both age groups had the same median score (IQR) of 3.00 (3.00-6.00) at baseline (p=0.890) and the same median score (IQR) of 3.00 (0.00-3.00) following supplementation (p=0.787). Age did not, thus, influence the median score within the active group subjected to the supplementation.

The active group was split into males (n=13) and females (n=17), and their responses were compared. Both groups had the same median score (IQR) of 3.00 (3.00-6.00) at baseline (p=0.765) and the same median score (IQR) of 3.00 (0.00-3.00) following supplementation (p=0.755). Sex did not, thus, influence the median score within the active group following supplementation.

The patients were again divided according to their PVD status into PVD (n=12) and no PVD (n=18) subgroups, and their median scores were compared. PVD in this case referred to the subjects with complete posterior vitreous detachment, which was observed in the biomicroscopy with the aid of the optical coherent tomography (OCT) and in the slit lamp. Both subgroups had the same median score (IQR) of 3.00 (3.00-6.00) at baseline (p=0.890). Following supplementation, the median scores (IQR) reported were 0.00 (0.00-3.00) and 3.00 (1.50-3.00) for the PVD and no PVD subgroups, respectively, but the difference was not statistically significant (p=0.213).

Changes in Visual Functions in the Active and Control Groups Before and After Supplementation The binocular contrast threshold was tested to assess the binocular contrast sensitivity pre and post supplementation, in order to assess the impact of vitreous floaters and the supplementation on the overall contrast sensitivity. It was observed for the active group that there is an improvement tendency in all conducted contrast sensitivity tests. The control group had varying results relating both to increases as well as decreases in contrast sensitivity at the end of the 6-month study period. Comparisons within groups showed statistically significant improvement on the MultiQuity LogCS scale (p=0.009) in the active group, whereas in the control group no improvement has been observed (p=0.855). A trend has also been observed towards the improvement of contrast sensitivity in the binocular contrast thresholds measured for the active group, but not for the control group. See Table 3 below.

16

Question: When during the day are the floaters most bothersome for you: in the morning, afternoon, evening or never?

Assess and tick the appropriate:
  0. never
  1. once a day (either in the morning, or in the afternoon, or in the evening)
  2. twice a day (when two times of the day are indicated)

TABLE 3

Comparison of the changes in visual functions in the active and control groups before and after supplementation.

| Visual function measures | CONTROL GROUP (placebo) | | | ACTIVE GROUP (supplemented with the composition according to the present invention) | | |
|---|---|---|---|---|---|---|
| | Baseline [Median (IQR)] | Final [Median (IQR)] | Sig. | Baseline [Median (IQR)] | Final [Median (IQR)] | Sig. |
| CS record result | 1.50 (1.40-1.90) | 1.80 (1.40-1.90) | 0.855 | 1.50 (1.30-1.88) | 1.80 (1.45-1.90) | 0.009* |
| Positive photopic FCS | 14.97 (11.73-26.38) | 15.18 (10.73-23.01) | 0.551 | 18.55 (10.15-29.89) | 14.94 (9.87-25.02) | 0.053 |
| Negative photopic FCS | 13.56 (9.46-31.56) | 12.79 (9.77-18.40) | 0.517 | 15.84 (8.87-29.55) | 14.08 (9.61-24.19) | 0.239 |
| Positive mesopic FCS | 71.42 (54.65-105.38) | 73.11 (56.07-92.02) | 0.563 | 78.28 (52.12-98.12) | 70.04 (43.42-100.92 | 0.191 |
| Negative mesopic FCS | 64.93 (46.76-81.13) | 59.00 (40.95-82.05) | 0.201 | 65.37 (36.34-83.59) | 57.29 (32.64-94.21) | 0.982 |
| MPOD 0.51° | 0.33 (0.24-0.47) | 0.37 (0.24-0.47) | 0.168 | 0.36 (0.26-0.45) | 0.36 (0.27-0.47) | 0.006* |
| MP size | 5034.00 (3119.50-6619) | 4992.00 (2971.50-6208.50) | 0.150 | 4795.50 (2870.75-6266.50) | 5296.00 (2767.25-6427.25) | 0.753 |

IQR—Interquartile range
Sig.—the statistical difference between the two time points
CS—Contrast Sensitivity
FCS—Functional Contrast Sensitivity
FCS measurements are registered as contrast threshold (%)
*statistically significant difference between two time points in the range of 0.05
MPOD—Macular Pigment Optical Density
MP—Macular Pigment Assessment Questionnaire of the Quality of Life in the Patients with Vitreous Floaters The questionnaire should be assessed by a clinician. The questionnaire is adapted to assess the functional disturbances of vitreous floaters.

Name:
Sex:
Birthdate:
Theme 1: Eyes with vitreous floaters
Question: Which of your eyes has vitreous floaters: right eye, left eye or both?
Tick the appropriate:
  a. Right eye
  b. Left eye
  c. Both eyes
Skip to theme 3 if floaters are present in one eye only.
Theme 2: The eye suffering from greater floater disturbances
Question: Which of your eyes bothers you more: the right or the left?
Tick the appropriate:
  a. Right eye
  b. Left eye
Theme 3: Frequency of floater disturbances during the day 3. all the time (when floaters appear in the morning, afternoon and evening)
Score=
Theme 4: Impact of vitreous floaters on daily life
Question: How would you describe the impact of vitreous floaters on your daily life in the course of the past week: no impact, a small impact, a moderate impact, a significant impact, a great impact?
Assess and tick the appropriate:
  0. no impact
  1. small impact
  2. moderate impact
  3. significant impact
  4. great impact
Score=
Theme 5: Activities affected by vitreous floaters
Question: Do vitreous floaters impair the below activities?
Score: Yes=1, No=0
  a. reading small prints (drug or cosmetics information leaflets)
  b. reading newspapers or books
  c. driving a car during the day
  d. using a computer or a mobile phone
  e. watching TV Score=

Theme 6: Degree of floater disturbances in the course of the past 6 months

Question: How can you describe the degree of floater disturbances in the course of the past 6 months?

My condition has been stable and I have not been bothered by my floaters

My floaters appear occasionally and are moderately bothersome

My floaters appear all the time and are consistently bothersome

Score for the floater disturbance=

CONCLUSIONS

The supplementation with the composition according to the present invention improves the subjective assessment of the quality of life of persons suffering from vitreous floaters. Simultaneously, unexpectedly for the inventors, after 6 months of conducting studies, there has been observed the significant improvement of the contrast sensitivity in the active group which received the composition of the dietary supplement according to the present invention and a lack of a relevant change in the control group which was given the placebo. The significant improvement of the contrast sensitivity in the active group which received the composition of the dietary supplement according to the present invention was statistically relevant in comparison with the group which did not receive this composition. The performance of the composition of the dietary supplement is not affected by age, sex and the presence and development stage of posterior vitreous detachment (PVD). During the 6-month supplementation period with the composition according to the present invention, persons from the active group did not report any side-effects of the studied composition.

Due to the conducted studies, the inventors unexpectedly observed that the consumption of the composition of the dietary supplement and/or nutritional additive for food according to the present invention significantly improves the subjective assessment of the quality of life in persons suffering from vitreous floaters.

Simultaneously, after the 6-month supplementation period with the composition according to the present invention, there has been observed the clearly detectable and significant improvement of the quality of visual performance in these patients through the significant improvement of the contrast sensitivity.

The present invention provides the composition of nutritional substances for oral administration, which positively impacts the quality of vision and contrast sensitivity in persons suffering from vitreous floaters.

Simultaneously, basing on the general knowledge on and experience in pathomechanisms, the course and development of various eye diseases, and the knowledge on the properties of the active substances used in the composition according to the present invention, and basing on the studies conducted for the purpose of the present invention and described above, which related to persons suffering from vitreous floaters, it is claimed that the developed composition and the unitary dosage form according to the present invention are suitable to provide a similar positive therapeutic effect and be used also in treating other different eye diseases and/or slowing down their development and/or inhibiting their development and/or preventing them, as well as, more generally, to be used with the aim to improve the quality of visual performance including contrast sensitivity in all persons in need of such an improvement, and with the aim to improve the quality of life of these persons.

The invention claimed is:

1. A method of treating persons suffering from vitreous floaters, which comprises using a composition of a dietary supplement and/or nutritional additive for food comprising L-lysine, vitamin C, zinc, grape extract and bitter orange extract in therapeutically effective quantities as active substances, and potentially at least one excipient, wherein percentages of the individual active substances relative to a sum of percentages of all active substances are:
   a) about 50% by weight of L-lysine,
   b) about 15% by weight of vitamin C,
   c) about 2% by weight of zinc,
   d) about 10% by weight of the grape extract,
   e) about 23% by weight of the bitter orange extract,
with all percentages of the individual active substances adding up to 100% by weight of all active substances.

2. The method according to claim 1, wherein the composition comprises:
   a) from about 125 mg to about 250 mg of L-lysine,
   b) from about 40 mg to about 80 mg of vitamin C,
   c) from about 5 mg to about 10 mg of zinc,
   d) from about 25 mg to about 50 mg of the grape extract,
   e) from about 60 mg to about 120 mg of the bitter orange extract.

3. The method according to claim 1, wherein the ingredients constitute a mixture.

4. The method according to claim 1, wherein the grape extract and/or the bitter orange extract are selected from the group comprising the extract of fruit seeds, the extract of fruit pulp, the extract of fruit skin, the extract of blossoms of these plants, or their combinations.

5. The method according to claim 1, wherein the grape extract is a grape extract of the *Vitis vinifera* species and/or the bitter orange extract is a bitter orange extract of *Citrus aurantium* species.

6. The method according to claim 1, wherein the excipient is a substance nutritionally permitted and is selected from the group consisting of at least a vehicle agent, a bulking agent, a binding agent, a disintegrant, a surfactant, a lubricant, an anti-caking agent, an acidity regulator, an antioxidant, a synthetic and/or natural colourant, a colour retaining substance, an emulsifier, a sweetener, an aromatizing agent, a flavouring agent, a flavour enhancer, a preservative, a stabilizing agent, a solvent, a diluent, and their mixtures.

7. The method according to claim 1, wherein the composition is formed as a powder, a granulate, a liquid, or a gel of any formulation adequate for oral application.

8. The method according to claim 1, wherein the composition is applied in a predetermined dose, frequency and a form for a period of at least 2 months.

9. The method according to claim 1, wherein the composition is formed into a unitary dosage form containing a daily dose of the active substances of the present composition.

10. The method according to claim 9, wherein the unitary dosage form is further prepared in a form selected from the group consisting of at least a capsule, a tablet, a sachet, a "stick-type" sachet and an ampoule, including any of the forms ensuring a prolonged release of the active substances of the composition in time of at least 3 hours after consumption.

11. The method according to claim 5, wherein the grape extract has a drug extract ratio (DER) of 100:1 and the bitter orange extract has a drug extract ratio (DER) of 100:1.

* * * * *